United States Patent
Montenegro et al.

(10) Patent No.: US 10,207,022 B2
(45) Date of Patent: Feb. 19, 2019

(54) CHITOSAN TISSUE DRESSING

(75) Inventors: Rivelino Montenegro, Mainz (DE);
Thomas Freier, Mainz (DE)

(73) Assignee: MEDODERM GMBH, Mainz (DE)

(\*) Notice: Subject to any disclaimer, the term of this patent is extended or adjusted under 35 U.S.C. 154(b) by 371 days.

(21) Appl. No.: 13/393,006

(22) PCT Filed: Sep. 1, 2009

(86) PCT No.: PCT/EP2009/006323
§ 371 (c)(1),
(2), (4) Date: May 7, 2012

(87) PCT Pub. No.: WO2011/026498
PCT Pub. Date: Mar. 10, 2011

(65) Prior Publication Data
US 2012/0215149 A1    Aug. 23, 2012

(51) Int. Cl.
*A61L 26/00* (2006.01)
*A61L 15/28* (2006.01)

(52) U.S. Cl.
CPC .......... *A61L 26/0023* (2013.01); *A61L 15/28* (2013.01); *A61L 26/0066* (2013.01); *A61L 2300/232* (2013.01); *A61L 2300/404* (2013.01)

(58) Field of Classification Search
CPC ...................................................... A61F 13/02
USPC .............. 602/41–42, 48–49; 424/43–47; 604/304–309; 606/213–221; 523/105–118
See application file for complete search history.

(56) References Cited

U.S. PATENT DOCUMENTS

| | | | |
|---|---|---|---|
| 4,532,134 A | 7/1985 | Malette et al. | |
| 8,303,980 B2* | 11/2012 | Hirose | A61K 36/899 424/443 |
| 2003/0022573 A1 | 1/2003 | Cintio et al. | |
| 2005/0042265 A1 | 2/2005 | Guillot et al. | |
| 2007/0254016 A1* | 11/2007 | Andersen | A61K 9/122 424/443 |
| 2010/0291055 A1* | 11/2010 | Athanasiadis | A61L 26/0052 424/94.1 |
| 2011/0264237 A1* | 10/2011 | Bayon | A61F 2/08 623/23.75 |

FOREIGN PATENT DOCUMENTS

| | | |
|---|---|---|
| EP | 0901795 A2 | 3/1999 |
| EP | 1396514 A1 | 3/2004 |
| GB | 2129300 A | 5/1984 |

(Continued)

OTHER PUBLICATIONS

Chitin-based tubes for tissue engineering in the nervous system.. Thomas Freiera,b, Rivelino Montenegroc, Hui Shan Koha,b, Molly S. Shoichet a,b,d..aDepartment of Chemical Engineering and Applied Chemistry, University of Toronto, 200 College Street, Toronto, Ont., Canada M5S 3E5 bInstitute of Biomaterials and Biom.. available on line Jan. 13, 2005.*

(Continued)

*Primary Examiner* — Tarla R Patel
(74) *Attorney, Agent, or Firm* — Harris Beach PLLC

(57) ABSTRACT

A tissue dressing material for being applied in contact with a tissue of a patient. The tissue dressing material's main component is deacetylated native chitosan. Moreover, a liquid tissue dressing material for being applied in contact with a tissue of a patient, the tissue dressing material being an aqueous mixture. The main component of the constituent(s) of the mixture other than water is deacetylated native chitosan.

16 Claims, 5 Drawing Sheets

(56) References Cited

FOREIGN PATENT DOCUMENTS

| JP | S598824 A | 1/1984 |
| JP | H1146909 | 6/1999 |
| JP | 2005517043 A | 6/2005 |
| JP | 2006347999 A | 12/2006 |
| JP | 2008161502 A | 7/2008 |
| WO | WO-2005087280 A1 | 9/2005 |
| WO | WO-2009028965 A1 | 3/2009 |

OTHER PUBLICATIONS

Preparation and biological activities of chitosan from the larvae of housefly, Musca domestica..Hui Ai, Furong Wang, Qiusheng Yang, Fen Zhu, Chaoliang Lei . . . College of plant science and technology, Huazhong Agricultural University, Wuhan 430070, P R China; Available online Sep. 19, 2007.*

Office Action in corresponding Canadian Patent Application No. 2,771,365 dated Jan. 28, 2014 (3 pages).

International Search Report and Written Opinion of the International Searching Authority for International Patent Application PCT/EP09/06323 dated May 17, 2010 (10 pages).

Minagawa, Tatsuya et al., "Effects of molecular weight and deacetylation degree of chitin/chitosan on wound healing", 2007 Carbohydrate Polymers 67 (pp. 640-644).

Kim, In-Yong et al., "Chitosan and its derivatives for tissue engineering applications," 2008 Biotechnology Advances 26 (pp. 1-21).

Japan Patent Office—Final Office Action for Patent Application No. 2012-525885 dated Jan. 6, 2015 (6 pages).

* cited by examiner

CHITOSAN TISSUE DRESSING

FIELD OF THE INVENTION

The invention relates to a tissue dressing material for being applied in contact with a tissue of a patient. It further relates to a tissue dressing material, in particular in a liquid or solid phase. Moreover, the invention relates to methods of treating a tissue of a patient, to a kit comprising a tissue dressing material, and to a use of a polymer with an antibacterial property.

BACKGROUND OF THE INVENTION

The polysaccharide chitosan is the at least partially N-deacetylated derivative of chitin. Chitin can be found widely in the exoskeletons of arthropods, shells, crustaceans and the cuticles of insects. It is usually derived from such natural sources. Chitosan in general is synthetically prepared by hydrolysis of chitin, although it can also be naturally derived directly, e.g. from certain fungi in which it occurs. The different solubilities of chitin and chitosan in dilute acids are commonly used to distinguish between the two polysaccharides. Chitosan, the soluble form, can have a degree of acetylation (DA) between 0% and about 60%, the upper limit depending on parameters such as processing conditions, molecular weight, and solvent characteristics. While soluble in acidic aqueous media, chitosan precipitates at a pH of above 6.3.

Both chitin and chitosan are promising polymers for biomedical applications because of their biocompatibility, biodegradability and structural similarity to the glycosaminoglycans. For comprehensive reviews of potential applications of chitin and chitosan see, e.g., Shigemasa and Minami, "Applications of chitin and chitosan for biomaterials", Biotech. Genetic. Eng. Rev. 1996, 13, 383; Kumar, "A review of chitin and chitosan applications", React. Funct. Polym. 2000, 46(1), 1; and Singh and Ray, "Biomedical applications of chitin, chitosan and their derivatives", J. Macromol. Sci. 2000, C40(1), 69.

Chitin and chitosan have been held to be of particular promise in wound healing applications, early scientific reports on this subject dating back to 1970 when Prudden et. al. in "The discovery of a potent pure chemical wound-healing accelerator", Am. J. Surg. 1970, 119, 560 described the successful application of chitin powder on human wounds. The primary factor in the acceleration of wound healing was reported to be the presence of N-acetyl-D-glucosamine (in contrast to D-glucosamine) which is released from chitin due to enzymatic degradation by lysozyme, which is abundantly available in fresh and healing wounds.

The use of poly(N-acetyl-D-glucosamine), i.e. chitin, as a wound healing accelerator is disclosed in the U.S. Pat. No. 3,632,754. U.S. Pat. No. 4,532,134 discloses the application of chitosan solutions, powders, films, and mats to wounds. The claimed method asks for chitosan being between 42 to 100% deacetylated. Animal experiments using 78 to 92% deacetylated chitosan are disclosed that show acceptable results when the material is applied to wounds of dogs, while interference with early wound healing is observed when the material is used to cover wounds of rats.

In the U.S. Pat. No. 5,902,798 and the US patent application 2001/0056079 degrees of acetylation of less than 25% are asked for. In experiments applying 16% acetylated chitosan, inferior stimulation of cell proliferation and wound healing were found in an in vitro model using human skin compared to chitosan/heparin materials.

The UK patent GB 2358354 B teaches a flexible polymeric film comprising at least 80% by weight of chitosan with a degree of acetylation between 12 and 30%. A slightly higher rate of wound healing compared to non-treated wounds was found. The relatively weak mechanical properties which necessitate the use of an epichlorhydrine cross-linker or silicon coating may constitute a disadvantage of this prior art material. The document also suggests washing off the film in saline solution after healing of the wound.

Azad et. al., "Chitosan membranes as a wound-healing dressing: Characterization and clinical application", J. Biomed. Mater. Res. 2004, 69B, 216, discloses the use of 25% acetylated chitosan for the fabrication of films and meshes (perforated films). The authors found that chitosan films cause an impaired wound healing in patients undergoing skin grafting as a result of blood clot formation underneath the film, while the use of meshes led to a more efficient removal of blood, resulting in faster healing with good epithelialization and without scar formation.

In the U.S. Pat. No. 7,482,503 a chitosan acetate foam is described for use as a hemorrhage control wound dressing for severe bleeding. The chitosan is required to be at least 70% deacetylated and in the examples, degrees of deacetylation between 85 and 93% are used.

The US patent application 2005/042265 A1 discloses a hydrogel for skin repair, the hydrogel containing a maximum of 5% chitosan. The chitosan's degree of acetylation is required to be no greater than 40%, in particular between 2% and 6%. Finally, the international patent application WO 2008/128567 A1 discloses medical articles, including wound dressings, at least partially made of chitosan. The lowest degree of acetylation disclosed is 3%.

Problem to be Solved by the Invention

It is an objective of the present invention to provide an improved tissue dressing material for being applied in contact with a tissue of a patient, an improved liquid tissue dressing material, and an improved tissue dressing. The inventions further aims to provide improved methods for treating a tissue of a patient, a new kit comprising a tissue dressing material, and a new use of a polymer with an antibacterial property.

Solution According to the Invention

According to the invention, the problem is solved by providing a tissue dressing material for being applied in contact with a tissue of a patient, wherein the tissue dressing material's main component is deacetylated native chitosan. Moreover, the problem is solved by providing a liquid tissue dressing material for being applied in contact with a tissue of a patient, the tissue dressing material being an aqueous mixture, wherein the main component of the constituent(s) of the mixture other than water is deacetylated native chitosan.

The problem is also solved by providing a tissue dressing comprising a first layer, which layer is formed of the tissue dressing material according to the invention, and another layer formed of another material. Moreover, the problem is solved by a method of treating a tissue of a patient, wherein a tissue dressing material is applied in contact with the tissue of the patient, the tissue dressing material's main component being deacetylated native chitosan. The problem is further solved by providing a method of treating a tissue of a patient, wherein a liquid tissue dressing material is applied in contact with the tissue of the patient, the tissue dressing material being an aqueous mixture, and the main component of the constituent(s) of the mixture other than water being deacetylated native chitosan.

The problem is also solved by a method of treating a tissue of a patient, the method comprising the steps of: bringing a tissue dressing material into contact with the tissue, wherein the tissue dressing material comprises deacetylated chitosan; and applying a detachment solvent to the tissue dressing material. Further, the problem is solved by providing a kit comprising: a tissue dressing material, the tissue dressing material comprising chitosan, and a detachment solvent.

Finally, the problem is solved by the use of a polymer with an antibacterial property for the locally confined antibacterial treatment of a patient's tissue.

In the context of the present invention, the expression "main component" with regard to the tissue dressing material and a type of chitosan (such as chitosan in general, deacetylated chitosan, native chitosan or deacetylated native chitosan) means that the respective type of chitosan makes up at least 50% by weight of the tissue dressing material. Thus, if e.g. the tissue dressing material is provided as a solid or gel-like film to be applied to the tissue, this film is required to be made up of the respective type of chitosan by at least 50% by weight. In the case of the liquid tissue dressing material, the expression "main component" with regard to the constituent(s) other than water in the aqueous mixture means that at least 50% by weight of the combination of all constituents other than water must be the respective type of chitosan. Also, as discussed further below, the tissue dressing may comprise a first layer, which layer is formed of the tissue dressing material, and another layer formed of another material, this other layer acting as a support. In such a case, according to the above definition, it would be the first layer but not the support layer that is required to be made up of the respective type of chitosan by at least 50% by weight. Note that material which the tissue dressing material takes up from a tissue, such as exudative fluid from a wound, is not considered a component of the tissue dressing material.

The term "native chitosan", in the context of the present invention refers to the defined chemical entity chitosan, which is a poly(N-acetyl-D-glucosamine-co-D-glucosamine) copolymer or a poly(D-glucosamine) homopolymer. Any cross-linked or otherwise chemically modified chitosan is considered a chitosan derivative, having different properties than native chitosan. In the context of the present invention the term "native chitosan" includes both the chitosan base and chitosan in the form of a chitosan salt, dissolved or un-dissolved. When in the context of the present invention it is referred to "chitosan" in general, this can be native chitosan or any derivative of a poly(N-acetyl-D-glucosamine-co-D-glucosamine) copolymer or a poly(D-glucosamine) homopolymer, cross-linked and/or otherwise modified.

In the context of the present invention the term "deacetylated chitosan" means that the chitosan's degree of acetylation (DA) is less than 2.5%. The DA can be obtained by means of $^1$H NMR spectroscopy as, e.g., disclosed in Lavertu et al., "A validated $^1$H NMR method for the determination of the degree of deacetylation of chitosan", J Pharm Biomed Anal 2003, 32, 1149. "Deacetylated native chitosan" in the context of the present invention refers to chitosan that is both native and deacetylated according to the above definitions.

The tissue dressing material according to the invention can advantageously be employed as a wound dressing material. In certain aspects, the invention exploits the inventors' discovery that a significantly accelerated rate of wound healing can be achieved by applying a native chitosan material that is deacetylated, i.e. essentially free of N-acetyl-D-glucosamine subunits. This finding is surprising when considering the importance attributed to the N-acetylated form of D-glucosamine in wound healing applications, e.g. as described in the U.S. Pat. No. 3,632,754, supra. Furthermore, it has been suggested, e.g., in Izume et. al., "A novel cell culture matrix composed of chitosan and collagen complex", in: Chitin and chitosan, Amsterdam 1989, 653, that chitosan of a very low degree of acetylation may rather have cytostatic properties, as it inhibits cell proliferation due to an extremely high cell adhesion.

Therefore, with the invention improved wound healing properties such as an accelerated wound healing can be achieved. Other attainable advantages of the invention include the maintenance of a sufficient degree of humidity at the wound site, the absorption of exudative fluids and toxins, adequate gas exchange, and thermal insulation.

Also, in some aspects the invention exploits the fact that chitosan is dissolvable in acidic aqueous media. The terms "dissolvable" and "dissolution" refer to a process of mass loss of a solid chitosan form without molecular weight decrease (ie, without decrease in polymer chain length) due to solubility in an aqueous environment. This is to be distinguished from "degradation", which is the process of molecular weight decrease due to depolymerisation of chitosan. Advantageously dissolution can facilitate the removal of the tissue dressing material. It can be achieved with the invention that the tissue dressing material is partly or even entirely dissolvable.

Advantageously, the tissue dressing material according to the invention can have a high biocompatibility and bioactivity, in particular through the use of deacetylated native chitosan. In contrast, cross-linking of chitosan, either non-covalently or covalently, may lead to the blockage of active functionalities of the biomaterial, namely the amine groups. Prior art chitosans that are cross-linked or otherwise chemically modified may therefore carry the risk of limited biocompatibility and loss of functionality, such as cell adhesiveness and growth, antibacterial properties, hemostatic properties, as well as the ability to biodissolve or biodegrade partially or completely and into non-toxic components.

Further advantageously, with the invention a tissue dressing material can be provided that is essentially free of toxic compounds. The invention can reduce the risk of wound infections, by exploiting the antibiotic nature of the deacetylated native chitosan as a natural polymeric antibiotic with no systemic but only topical activity. Moreover, by virtue of the low DA of the deacetylated native chitosan, the tissue dressing material can be applied in practically non-lysozyme biodegradable form, which can contribute to preventing tissue ingrowths and undesired adhesion of the polymeric matrix to growing tissue. Also, the removal of the tissue dressing can be facilitated, and the irritation or damage of the regenerating tissue due to adhesions to the wound dressing being removed can be avoided.

The liquid tissue dressing material according to the invention advantageously can exploit the fact that deacetylated native chitosan is soluble in such acidic aqueous media.

Advantageously, by applying the detachment solvent according to the invention, irritation or damage of the tissue to which the tissue dressing is attached can be avoided.

It is an attainable advantage of the use of a polymer with an antibacterial property according to the invention that a systemic antibacterial activity can be avoided, i.e. the antibacterial treatment of regions of the patient's body where such treatment is not required and/or not desirable. The invention can thus reduce side effects and contribute to the swift recovery of the patient.

PREFERRED EMBODIMENTS OF THE INVENTION

Preferred features of the invention which may be applied alone or in combination are discussed in the dependent claims and in the following description.

Preferably, the tissue dressing material is present in the form of a solid film or a gel-like film. The preferred film has a smooth surface, preferably with an average roughness $R_a$ of 1 μm (micrometer) or less, more preferably 0.3 μm or less, more preferably 0.1 μm or less. Advantageously, a smooth surface can reduce the formation of mechanical anchoring to the tissue, thereby making it easier to remove the dressing. Typically the film is between 5 and 500 μm (micrometers) thick, preferably between 10 and 100 μm. It has a surface area sufficient to cover the tissue to be treated, such as a wound, and, preferably, also some of the surrounding tissue.

Preferably, at least 70%, more preferably at least 90%, more preferably at least 95% by weight of the tissue dressing material is deacetylated chitosan, preferably deacetylated native chitosan. A preferred tissue dressing material entirely consists of deacetylated chitosan, preferably deacetylated native chitosan.

In certain embodiments of the invention, the tissue dressing material is present as a liquid aqueous mixture. Preferably, at least 70% by weight of the constituent(s) of the mixture other than water are deacetylated chitosan, preferably deacetylated native chitosan. A particularly preferred mixture essentially only consists of deacetylated chitosan, preferably deacetylated native chitosan, and water. The preferred mixture is acidic. The concentration of the deacetylated native chitosan preferably is less than 15%, more preferably less than 10%, more preferably less than 5%, more preferably less than 2% by weight. For application, the liquid dispersion preferably is sprayed or brushed onto the tissue and the dispersion medium subsequently is allowed to evaporate. As a result, a solid or gel-like film forms. Typically the film is between 1 and 50 μm (micrometers) thick, preferably between 10 and 20 μm. It has a surface area sufficient to cover the tissue to be treated, such as a wound, and, preferably, also some of the surrounding tissue.

In a preferred tissue dressing material according to the invention, the deacetylated chitosan's or the deacetylated native chitosan's DA is 2% or less, preferably 1.5% or less, more preferably 1% or less, more preferably 0.5% or less. Advantageously, such extremely low degrees of acetylation can further improve the wound healing properties of the invention. Also, biodegradation can be further inhibited, avoiding tissue ingrowths and excessive adhesion of the tissue dressing material.

In a preferred embodiment of the invention, the respective type of chitosan, preferably deacetylated native chitosan, is at least partly present in the form of a chitosan salt. It is an achievable advantage of this embodiment of the invention that the tissue dressing material adheres well to the tissue. Thereby, it can be avoided that the tissue dressing material prematurely detaches from the tissue. This embodiment of the invention advantageously exploits the fact that chitosan salt is soluble in an aqueous solvent of neutral pH. Thus, wet or pre-wetted tissue can liquefy the tissue dressing material's surface, providing for a durable contact with the tissue. Preferred salts are those derived from the dissolution of chitosan in inorganic acids, such as hydrochloric acid, and organic acids selected from the group of monobasic or multibasic organic acids having 2 to 12 carbon atoms and a first pKa value between 1 and 5, such as acetic acid, citric acid, lactic acid, malic acid, succinic acid, mandelic acid, oxalic acid, tartaric acid, ascorbic acid, etc. In an alternative embodiment of the invention the respective type of chitosan, preferably deacetylated native chitosan, is present in the form of the chitosan base.

The tissue dressing material in some embodiments of the invention is a mixture or a compound material, comprising other components in addition to the respective type of chitosan, preferably deacetylated native chitosan. In a preferred embodiment, the tissue dressing material comprises at least one pharmaceutically active and/or bioactive additional component. Suitable bioactive additional components may e.g. be proteins, peptides or derivatives thereof, nucleic acids or derivatives thereof, low molecular weight compounds active as drugs, such as antibiotics or anti-inflammatory drugs, or agonists or antagonists of the innate immune system, or stimulating or differentiating growth factors for stimulating or differentiating growth of at least one subtype of cells or resins with affinity to certain components to be extracted from a wound surface, or soluble or dispersed compounds or polymers with decorative functions such as light absorbing, fluorescent or phosphorescent dyes or light reflecting particles. Alternatively or in addition, the tissue dressing material may comprise biological cells.

The preferred tissue dressing material has a water uptake capacity of less than 100% by weight, more preferably less than 80%. Thereby, it is advantageously achievable that a degree of humidity that is favourable for wound healing can be maintained at a wound site.

Preferably, the tissue dressing material has a water uptake capacity of more than 25%, more preferably more than 50%. Advantageously, this embodiment of the invention is suitable for absorbing exudative fluids and toxins. In a particularly preferred embodiment of the invention, the water uptake capacity of the tissue dressing material is between 65% and 75%.

In a preferred embodiment of the invention, the tissue dressing material has a pH below 6.3, preferably below 6, particularly preferably around 5 to 5.5. The preferred pH is above 4.0, more preferably above 4.5. It is an achievable advantage of this embodiment of the invention, that the pH is close to that of the surface of healthy skin, thereby avoiding irritation or damage of the tissue to which the tissue dressing material is attached. This embodiment of the invention preferably applies to external applications of the tissue dressing material.

In a preferred embodiment of the invention, the tissue dressing material has a pH below 8.5, preferably below 8, particularly preferably around 7 to 7.5. The preferred pH is above 6.0, more preferably above 6.5. It is an achievable advantage of this embodiment of the invention, that the pH is close to that of healthy tissue, thereby avoiding irritation or damage of the tissue to which the tissue dressing material is attached. This embodiment of the invention preferably applies to internal applications of the tissue dressing material.

In a preferred embodiment of the invention, the tissue dressing material is transparent. Advantageously this can make it easier for a physician to inspect a wound treated with the tissue dressing material. In some embodiments, the material is a transparent solid film. In others, it is a dispersion that forms a transparent film when applied to the tissue.

A preferred tissue dressing according to the invention comprises a first layer, which layer is formed of the tissue dressing material, and another layer formed of another material, this other layer acting as a support. In particular, the support advantageously can help preventing premature detachment of the tissue dressing material from the tissue. The support preferably is located at the side of the layer of the tissue dressing material opposite to the side that is in contact with the tissue. Preferably, the support is adjacent to the tissue dressing material. The support according to the invention is particularly advantageous if the respective type of chitosan, preferably deacetylated native chitosan is provided in the tissue dressing material in the form of the chitosan base, as the chitosan base in general adheres less well to tissue than a chitosan salt containing tissue dressing material. The support may for example be a woven fabric. The support may for example be of natural materials such as cotton or a natural or synthetic polymer. Suitable polymers include biodegradable polymers, such as polyesters, polyorthoesters, polycarbonates, polyanhydrides, polyurethanes, polyphosphazenes, polyphosphoesters, polysaccharides, polypeptides, as well as derivatives, copolymers, and blends based on these polymers. Suitable polymers also include biodissolvable polymers, such as polyvinyl alcohol, polyvinyl acetate, poly-N-vinyl pyrrolidone, polyethylene glycol, polypropylene glycol, polysaccharides, polypeptides, as well as derivatives, copolymers, and blends based on these polymers. Furthermore, the support may consist of a non-biodegradable/non-biodissolvable polymer, such as silicones, polyurethanes, polyethylene terephthalate, polytetrafluorethylene, polysulfones, polyethersulfones, polyether ether ketones, polycarbonates, polymethacrylates, polysaccharides, polypeptides, as well as derivatives, copolymers, and blends based on these polymers.

A preferred tissue dressing according to the invention comprises a first layer, which layer is formed of the tissue dressing material, and another layer formed of another material, this other layer acting as an at least partial moisture barrier. In other words the other layer can prevent or at least delay the evaporation of water in the tissue dressing material during treatment of the tissue with the tissue dressing material according to the invention. The other layer preferably is located at the side of the layer of the tissue dressing material opposite to the side that is in contact with the tissue. Preferably, the other layer is adjacent to the tissue dressing material. The invention also encompasses tissue dressings that have both a support layer and another layer that acts as an at least partial moisture barrier. Of course both functions, that of a support and that of an at least partial moisture barrier, can also be fulfilled by a single other layer. The other layer may for example be of silicone or another polymer or polymer composition from the groups of polymers listed above. Typically the other layer is between 10 and 1000 µm thick, preferably between 50 and 500 µm. In some embodiments of the invention, the other layer is perforated. The holes of the perforation typically are between 10 and 1500 µm in diameter, preferably between 50 and 1000 µm.

In a preferred method of treating a tissue according to the invention, the tissue dressing material not only contacts the tissue to be treated but also tissue surrounding the tissue to be treated. While the tissue dressing material preferably is used for external wounds, it may also be applied to internal wounds. In a preferred method, the wound dressing is used internally as a hemostatic agent to control bleedings during surgeries, or it is applied in the treatment of injuries or diseases that cause internal bleedings. In another preferred method, the wound dressing is used internally to prevent or limit infections by exploiting the potential of the deacetylated native chitosan as polymeric antibiotic. In another preferred method, the wound dressing is used in regions of the body that are difficult to reach or treat, such as orifices, the genital area, or parts of the body where wound healing can be delayed, due to limited exposure to air. In a particularly preferred method, the wound dressing is applied in areas that are sensitive to the application of foreign-body materials and conventional wound dressings, such as mucosa. The material may be applied into or onto the wound.

The solubility of chitosan is exploited in the method according to the invention of treating a tissue of a patient, wherein in a first step the tissue dressing material is brought into contact with the tissue and in a second step a detachment solvent is applied to the tissue dressing material to at least partly dissolve the tissue dressing material. Advantageously, by applying a detachment solvent to the tissue dressing material, at least part of the tissue dressing material can be dissolved. Thereby, removal of the tissue dressing material from the tissue can be facilitated. In the step of at least partly dissolving the tissue dressing material, preferably at least part of the chitosan component of the tissue dressing material is dissolved.

The chitosan used together with the detachment solvent preferably is deacetylated native chitosan, even though the invention also encompasses methods in which the chitosan is a chitosan derivative. Preferably, the deacetylated chitosan, more preferably the deacetylated native chitosan, is the tissue dressing material's main component, more preferably the tissue dressing material is a material as described in one of the above embodiments.

A preferred kit according to the invention comprises a tissue dressing material for being applied in contact with a tissue of a patient, the tissue dressing material comprising chitosan. Preferably, the chitosan in the tissue dressing material is deacetylated chitosan. Preferably, the chitosan in the tissue dressing material is native chitosan, more prefer by deacetylated native chitosan. Preferably, the chitosan, more preferably the deacetylated chitosan, more preferably the deacetylated native chitosan, is the tissue dressing material's main component, more preferably the tissue dressing material is a material as described in one of the above embodiments. In some embodiments of the kit according to the invention, in addition to a layer of the tissue dressing material another layer as described above may be provided, e.g. as a support or as an at least partial moisture barrier. Moreover, a preferred kit according to the invention comprises a detachment solvent for at last partly dissolving the tissue dressing material to detach the tissue dressing material at least partly from the tissue. The amount of detachment solvent provided in the kit is at least 5 times per weight the amount of chitosan provided in the kit, more preferably at least 50 times per weight the amount of chitosan provided in the kit. By providing a sufficient amount of detachment solvent, it can be avoided that the pH of the tissue dressing material solution falls under a certain threshold. The detachment solvent may for example be provided in a sealed bottle or disposable pipette, or by means of a gauze, a sponge or a gel soaked with the detachment solvent.

Preferred detachment solvents include distilled water, aqueous solutions of ionic compounds, such as an aqueous sodium chloride solution, buffered solutions, such as an acetic acid/acetate buffered solution, as well as aqueous solutions of non-ionic compounds, such as an aqueous glucose solution. The preferred pH of the detachment solvent is around or below 7, more preferably below 6.5, more preferably below 6. The preferred pH of the detachment solvent is preferably above 3.5, more preferably above 4, more preferably above 4.5.

In the use according to the invention of a polymer with antibacterial property, the polymer preferably is provided in the form of a tissue dressing material according to the invention. Preferably, the material is solid or gel-like or assumes a solid or gel-like consistency when applied to the tissue. This embodiment of the invention exploits the fact that the site where the polymer is present and thus the antibiotic activity takes place can be well controlled for just a local presence of the antibiotic activity.

The tissue dressing material according to the invention advantageously can be applied to acute wounds, chronic wounds, and burn wounds or other types of wounds. It can also be applied to tissue affected by dermatosis, for example athlete's food disease and psoriasis. The tissue dressing material can be applied in wound coverings, for example band aids, gauzes, films and foams, and in support aids, for example bandages, support tights and plaster casts. The tissue dressing material and the tissue dressing according to the invention may advantageously be applied to treat cuts and abrasions, nose bleeding, severely bleeding wounds, and external and internal wounds in general. Thus, the invention can be of use when surgery is performed on a patient. The invention can also be applied advantageously to treat acne, razor burn and insect bites as well as in cosmetic application such as face masks and peelings.

The tissue dressing material according to the invention in particular can exhibit one or a combination of the following advantageous properties: transparency; adhesion to the tissue to which it is applied; permeability for gas, in particular oxygen; locally confined antibiotic properties; regulation of humidity; and dissolvability at moderate pH. The material may inhibit or, alternatively, promote the growth cells of the tissue treated. It may also act as a barrier to protect from bacterial infection from inside and outside the tissue treated and as a mechanical protection. In particular it may protect and cover superficial wounds, lesions, abrasions that are at risk of infection, and burns. The tissue dressing material and the tissue dressing according to the invention can provide protection in cases where conventional wound dressings prove ineffective or are at least less effective, such as in the treatment of ulcerous tissue, wounds caused by viruses which tend do become ulcerous, mucosal tissue, the genital area, and body cavities.

BRIEF DESCRIPTION OF THE DRAWINGS

The invention is illustrated in greater detail with the aid of the schematic drawings.

DETAILED DESCRIPTION OF EMBODIMENTS OF THE INVENTION

1H NMR Spectroscopy

Figure 1:
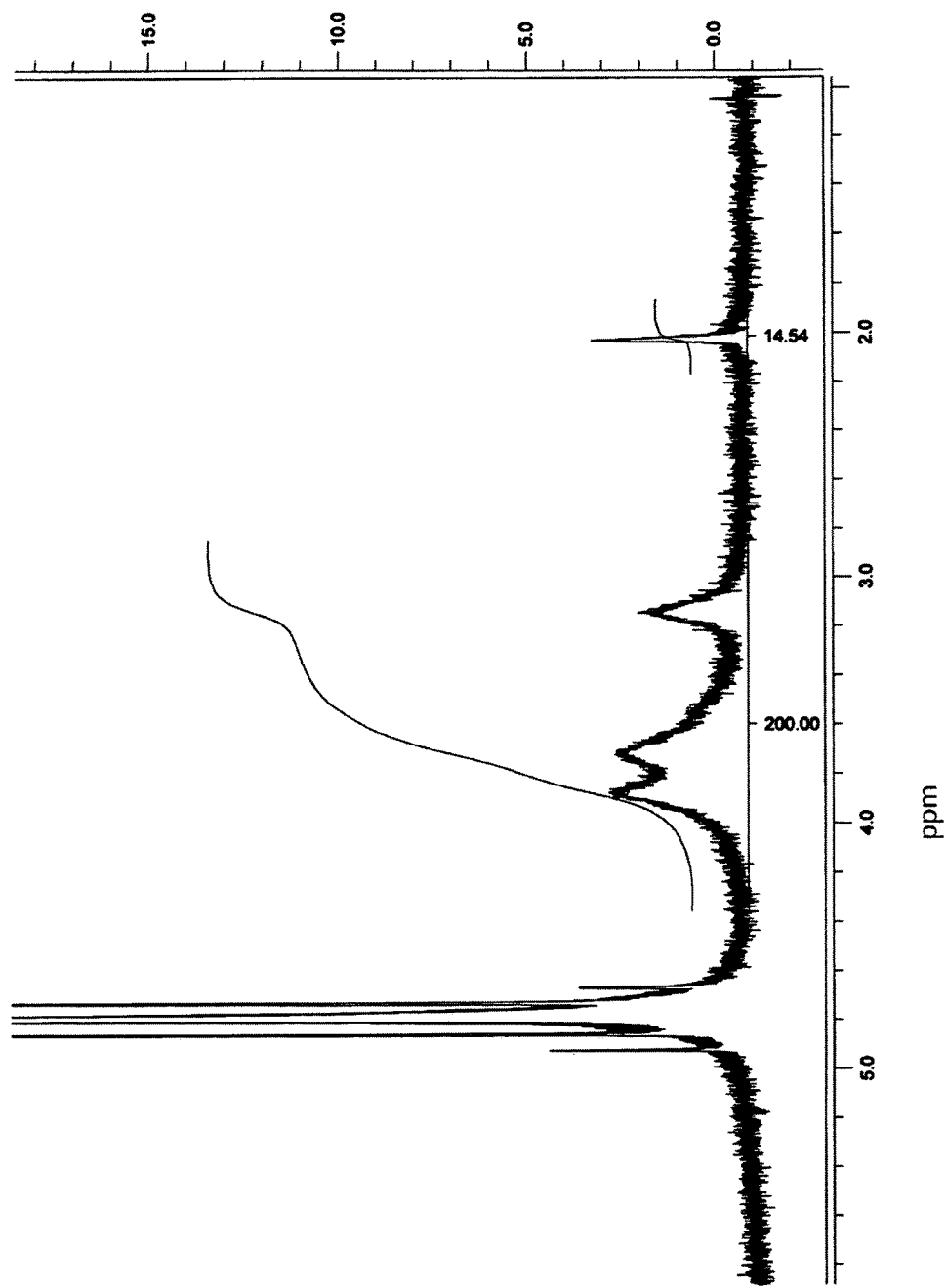
FIG. 1 shows an $^1$H NMR spectrum of native chitosan as purchased.
Figure 2:
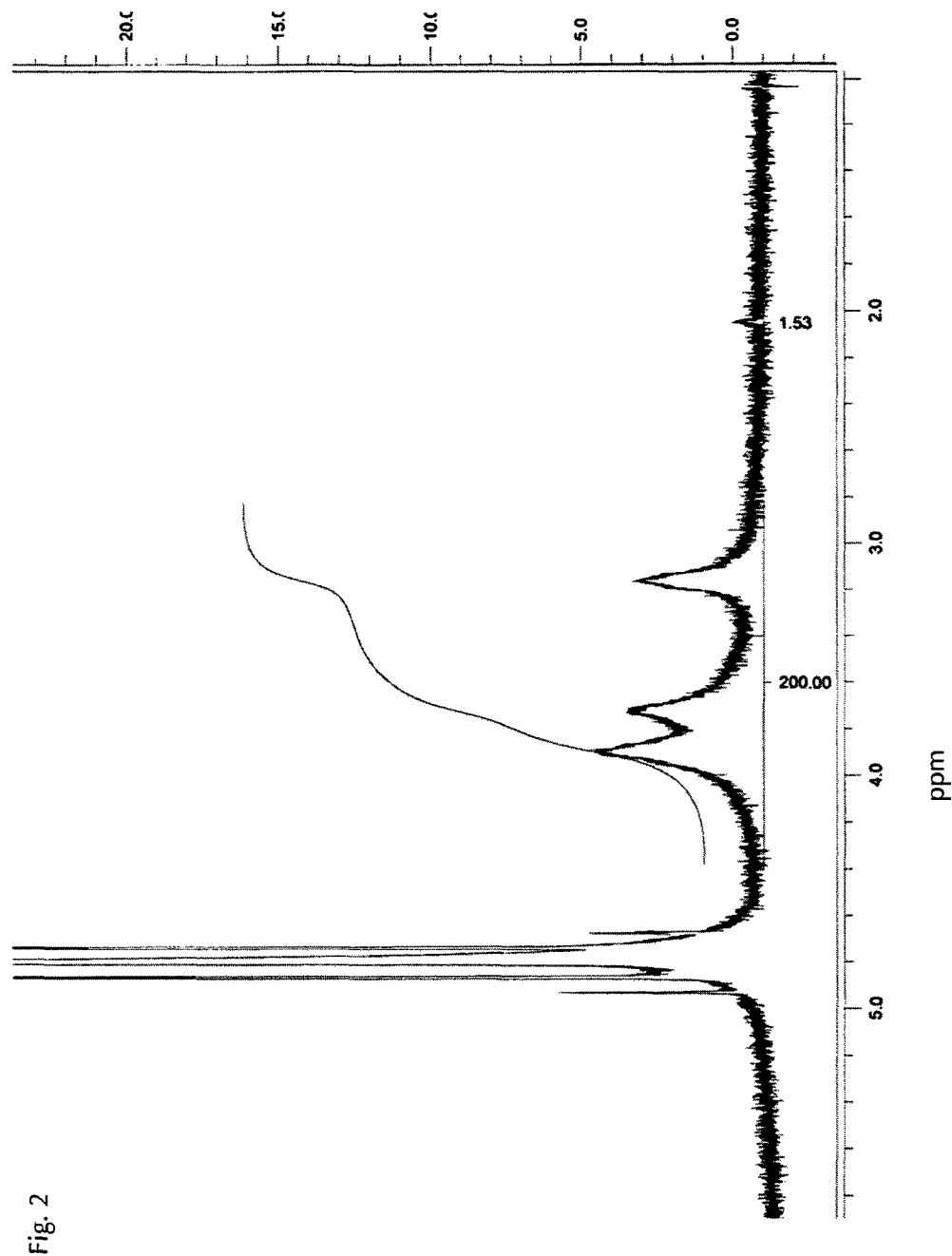
FIG. 2 shows an $^1$H NMR spectrum of native chitosan essentially deacetylated after further hydrolysis steps.

The chitosan used as a starting material in the examples below was obtained in the form of fine flakes from Cognis (Germany). The degree of acetylation (DA) was determined by $^1$H NMR spectroscopy. FIG. 1 shows an $^1$H NMR spectrum obtained from this commercially available chitosan. FIG. 2 shows a corresponding $^1$H NMR spectrum obtained from chitosan deacetylated after further hydrolysis steps applied to the commercial product as described further below. In both cases, chitosan was analyzed in a mixture of 0.25% DCl in $D_2O$ at a chitosan concentration of approximately 0.5% (w/v). The spectra were recorded using a Bruker AC200 spectrometer. NMR chemical shifts ($\delta$, in ppm) were referenced to the signal of HDO ($\delta$=4.8 ppm). The DA, calculated by comparing the integrated area under the peaks associated with H2-H6 of the D-glucosamine subunit with that of the methyl group, was determined as 14.5% for the native chitosan as purchased, and 1.5% for the deacetylated native chitosan.

Synthesis of Low-DA Chitosan

For further hydrolysis, 50 g (grams) of the chitosan flakes as obtained from the supplier Cognis were placed in a glass container, and 500 g of a 45% aqueous sodium hydroxide solution were added. The glass container was well shaken to mix the components, and placed in an oven for 2 hours at 100° C. It was then removed from the oven, and 500 ml (milliliters) of distilled water were added. The mixture was filtered through a glass frit. Then, the chitosan was washed with distilled water until the pH of the filtrate reached 6.5, and dried at 100° C. for 4 h (hours). This hydrolysis treatment was then repeated, resulting in 42 g of deacetylated native chitosan having a DA of 1.5% as determined by $^1$H NMR spectroscopy.

Cell Viability on Low-DA Chitosan

Human HaCaT keratinocytes were cultured in serum-free medium (Gibco) supplemented with 0.2 ng/ml (nanograms per milliliter) rEGF and 25 µg/ml (micrograms per milliliter) bovine pituitary extract. The calcium concentration was adjusted to 0.02 mM and the pH to 7.2-7.4. Cells were seeded at a density of $1 \times 10^6$ cells per 20 ml medium and incubated at 37° C. in air containing 10% $CO_2$. Cells were passaged once per week, and passages 20-25 were used for analysis.

Figure 3:
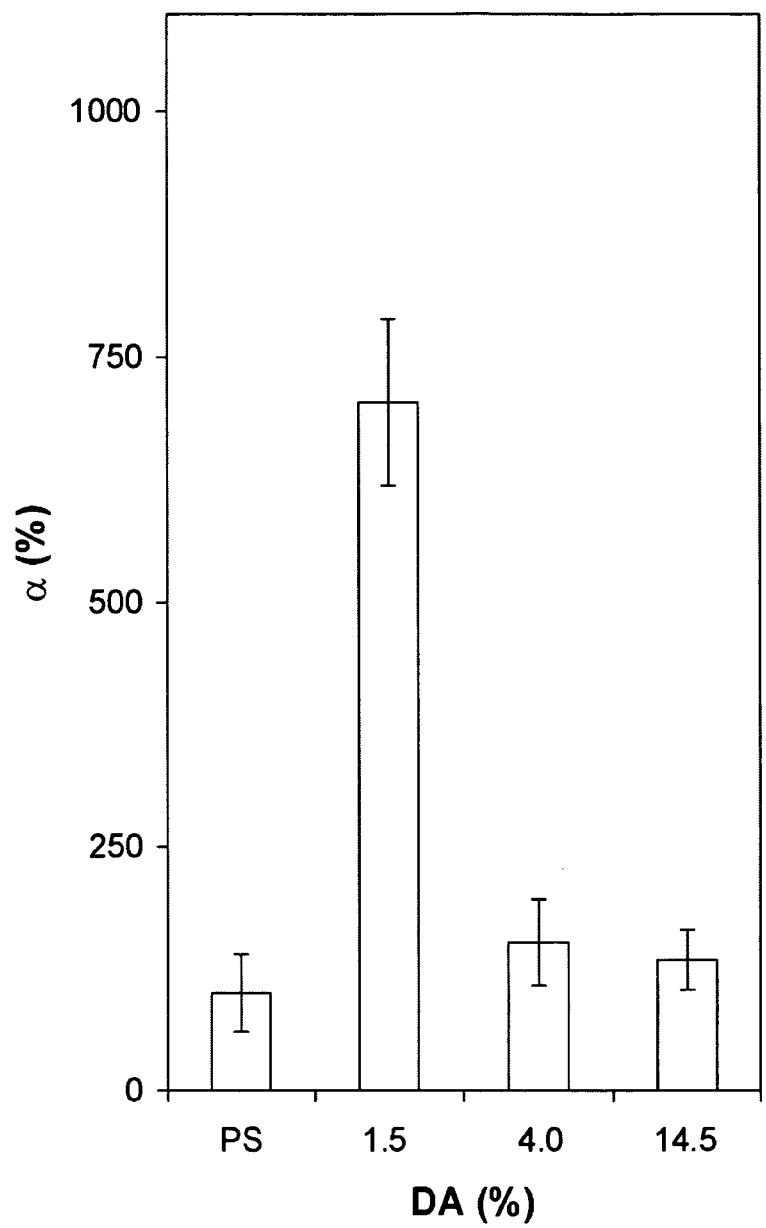
FIG. 3 illustrates the cell viability of keratinocytes on chitosan materials of various degrees of acetylation, relative to tissue culture polystyrene controls (PS=100%)

Chitosan films having DAs of 1.5, 4.0, and 14.5%, respectively, were placed in 24-well cell culture plates, and HaCaT keratinocytes were seeded at a density of $5 \times 10^4$ cells per $cm^2$ and cultured for 2 days. Cell viability was determined using the MTS assay (Promega). After 4 h of MTS incubation with the cells, the light absorbance at 490 nm was measured by an ELISA plate reader and subtracted from that of the controls (without cells) to yield the corrected absorbance. Five samples of each DA were studied. FIG. 3 shows the relative light absorbencies $\alpha$ at 490 nm (PS=100%) for the three samples and a control using polystyrene (PS).

Preparation of a Solution of the Tissue Dressing Material 7.5 g of the thus obtained native chitosan having a DA of 1.5% were dissolved in 500 ml of a 0.5% aqueous acetic acid by gently shaking for 24 h. A portion of the solution was filtered first through a glass fiber filter (pore size approximately 1 μm), and then through a 0.22 μm filter for sterilization, resulting in solution of a tissue dressing material essentially consisting entirely of deacetylated native chitosan. Below, the material is referred to as tissue dressing material A.

Preparation of a First Example of a Solid Film-Type Tissue Dressing Material

Two portions of 144 ml each of the non-filtered solution of deacetylated native chitosan prepared above were poured into two square-shaped moulds, 24×24 cm² (square centimeters) in size, and left in a dust-free environment for drying at room temperature. The resulting film was removed from the first mould, and sterilized using a 10 kGy (kilogray) electron beam. An approximately 80 μm thick transparent film of tissue dressing material essentially consisting entirely of deacetylated native chitosan acetate salt was obtained. Below, the material is referred to as tissue dressing material B.

Preparation of a Second Example of a Solid Film-Type Tissue Dressing Material

The dried film from the second mould was placed for 2 hours in a bath containing a solution of 1.5% ammonia in methanol/water 90/10 (v/v). The film was then removed from the bath and dried by storage at room temperature. The film was sterilized using a 10 kGy electron beam. An approximately 80 μm thick transparent film of tissue dressing material essentially consisting entirely of deacetylated native chitosan base was obtained. Below, the material is referred to as tissue dressing material C.

Water Uptake of Tissue Dressing Material

Tissue dressing material C, produced as described in the above example, was weighted, and then placed in distilled water for 15 min. The weight of the wet film was compared to the weight of the dry film, and the water uptake was determined to be 72% by weight.

Application of Tissue Dressing Material

In Table 1 below, the outcomes of treatments of patients with the three examples of tissue dressing materials are detailed. Material A was sprayed directly onto a wound and then left uncovered to allow the solvent to readily evaporate into the air. Materials B and C were applied as small cuts of the film-like material in direct contact with the wound. In the case of material B, the skin was pre-wetted before the application of the material. In all examples, the material was left uncovered after application.

TABLE 1

| Type of chitosan tissue dressing | Patient | Wound | Application of the dressing | Outcome |
| --- | --- | --- | --- | --- |
| A | female, 49 yrs (years) | cut of 3.5 cm length and 5 mm depth (finger), moderate bleeding | application of appr. 2 ml of tissue dressing A (one treatment) | skin incision completely closed after 24 h |
| B | male, 42 yrs | cut of 1.5 cm length and 3 mm depth (hand), weak bleeding | application of tissue dressing B (size 2 × 0.5 cm²) on pre-wetted skin (one treatment) | skin incision completely closed after 4 h |

TABLE 1-continued

| Type of chitosan tissue dressing | Patient | Wound | Application of the dressing | Outcome |
| --- | --- | --- | --- | --- |
| C | male, 57 yrs | praeputial inflammation | application of tissue dressing C (size 1.5 × 1.5 cm²) (treatment repeated after 24 h) | Wound and ulcus completely healed after 48 h |

Dissolution of Chitosan Tissue Dressing

Controlled dissolution of tissue dressing materials B and C was tested in dissolution experiments using distilled water, 0.9% aqueous sodium chloride solution, and 0.5% acetic acid/acetate buffered solution, respectively. The pH of the solutions was adjusted to the values indicated in Table 2 using appropriate amounts of 1 N hydrochloric acid or sodium hydroxide solutions. Materials B and C were cut into rectangular samples having dry weights between 5 and 10 mg each. A gauze soaked with a 100-fold per volume excess of the respective solution to the dry weight of the film was applied to each sample film and the time for complete film dissolution was recorded.

TABLE 2

| pH of the dissolution mixture | Material B (distilled water) | Material B (0.9% aqueous sodium chloride) | Material C (0.9% aqueous sodium chloride) | Material C (0.5% acetic acid/acetate buffer) |
| --- | --- | --- | --- | --- |
| 4.0 | n.a. | n.a. | n.d. | 0.5 h |
| 4.5 | n.a. | n.a. | n.d. | 0.5 h |
| 5.0 | n.a. | n.a. | n.d. | 2 h |
| 5.5 | 0.1 h | 0.5 h | n.d. | 4 h | n.a. = not analyzed
n.d. = no dissolution observed after 24 h

In the controlled dissolution experiment with tissue dressing material C and a mixture of 0.5% acetic acid/sodium acetate (right column in Table 2), the material was stained by storage in 0.01% aqueous indigocarmine solution for 1 hour for better visualization. Complete dissolution was observed after 30 minutes at pH 4.0 and 4.5, after 2 hours at pH 5.0, and after 4 hours at pH 5.5, respectively (data not shown).

Figure 4:
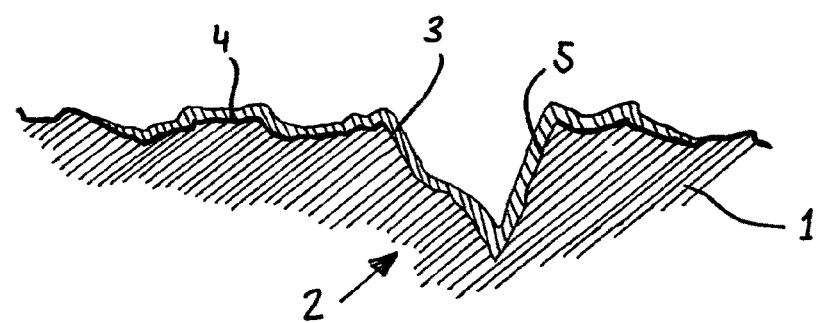
FIG. 4 schematically illustrates a wound to which a liquid tissue dressing material according to the inventions has been applied.

In FIG. 4, schematically a tissue 1, comprising a wound 2 is shown. For better illustration, FIGS. 4 to 7 are not drawn to scale. The liquid tissue dressing material according to the invention has been applied to the tissue 2 and the constituent water has been allowed to evaporate, leaving behind a film 3 that dresses the tissue 2 including the wound 3. In general, the film 3 is about 10 to 20 μm thick. Advantageously, the film 3 tightly snuggles to the tissue surface 4, including the wound surface 5.

Figure 5:
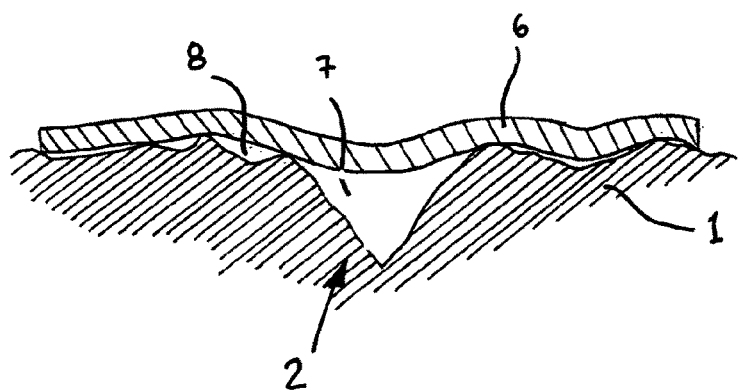
FIG. 5 schematically illustrates a wound to which a solid tissue dressing material according to the inventions has been applied.

FIG. 5 schematically shows a tissue dressing material in the form of a solid film 6 that is applied to a tissue 1, comprising a wound 2. The solid film is about 80 μm thick. Cavities 7, 8 between the tissue 1 and the tissue dressing material 6 may be filled with water or exudative fluid.

Figure 6:
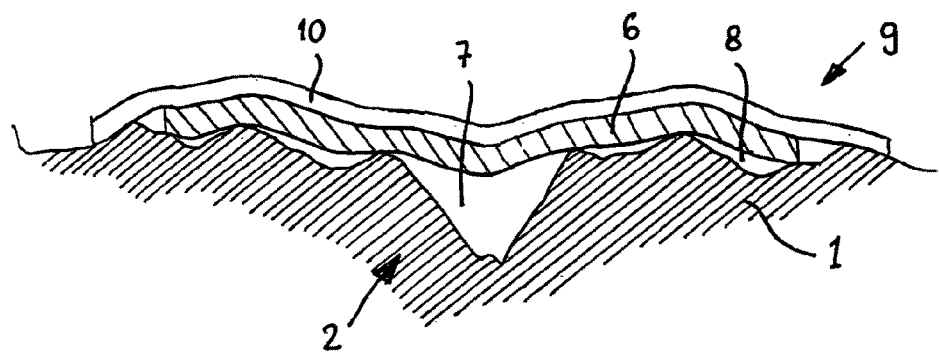
FIG. 6 schematically illustrates a wound to which a non-perforated wound dressing according to the invention has been applied.
Figure 7:
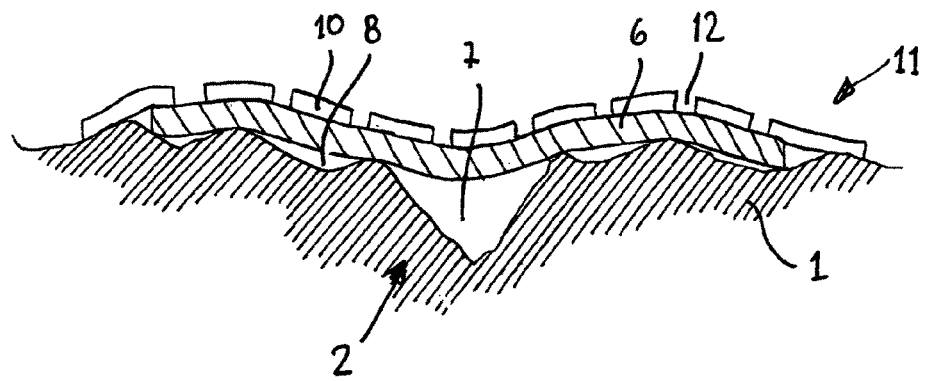
FIG. 7 schematically illustrates a wound to which a perforated wound dressing according to the invention has been applied.

In FIG. 6, a tissue dressing 9 comprising a tissue dressing material 6 of FIG. 5 as a first layer and a silicon film 10 as a second layer is applied to a tissue 1, comprising a wound 2. The silicon film 10 is about 50 μm tick. Again, Cavities 7, 8 between the tissue 1 and the tissue dressing material 6 may be filled with water or exudative fluid. Finally, FIG. 7 shows a tissue dressing 11 applied to a tissue 1 comprising a wound 2, the tissue dressing 11 differing from that 9 of FIG. 6 in that the silicon film 10 is perforated to allow an exchange of air between the tissue 1 and the surrounding though the wound dressing material 6. The perforations have a diameter if between 50 and 100 μm.

The features described in the above description, claims and figures can be relevant to the invention in any combination. The reference numerals in the claims have merely been introduced to facilitate reading of the claims and are by no means meant to be limiting.

The invention claimed is:

1. A tissue dressing material for being applied in contact with a tissue of a patient comprising at least 50% by weight native chitosan having a degree of acetylation below 2.5%, wherein the water uptake capacity of a solid phase of the tissue dressing material is less than 100% by weight.

2. The tissue dressing material according to claim 1, wherein the tissue dressing material is present in the form of a solid or gel-like film.

3. The tissue dressing material according to claim 1, wherein at least 70% by weight of the tissue dressing material is deacetylated native chitosan.

4. A liquid tissue dressing material for being applied in contact with a tissue of a patient, the tissue dressing material being an aqueous mixture comprising at least 50% by weight of the combination of all constituents other than water native chitosan having a degree of acetylation below 2.5%, wherein the tissue dressing material has a pH above 4.5.

5. The tissue dressing material according to claim 4, wherein at least 70% by weight of the constituent(s) of the mixture other than water is deacetylated native chitosan.

6. The tissue dressing material according to claim 1 or 4, wherein
the native chitosan's degree of acetylation is below or equal to 2%.

7. The tissue dressing material according to claim 1 or 4, wherein
the native chitosan is at least partly present as a chitosan salt.

8. The tissue dressing material according to claim 1 or 4, wherein
the tissue dressing material comprises at least one pharmaceutically active compound.

9. The tissue dressing material according to claim 1 or 4, wherein
the tissue dressing material has a pH below 6.3.

10. The tissue dressing material according to claim 1 or 4, wherein
the tissue dressing material is transparent.

11. A tissue dressing, comprising:
a first layer, which layer is formed of the tissue dressing material according to claim 1 or 4, and
another layer formed of another material.

12. The tissue dressing of claim 11, wherein
the other layer acts as a support.

13. The tissue dressing of claim 11, wherein
the other layer acts as an at least partial moisture barrier.

14. A method of treating a tissue of a patient, comprising a step of applying a tissue dressing material in contact with the tissue of the patient,
the tissue dressing material comprising at least 50% by weight native chitosan having a degree of acetylation below 2.5%,
wherein the water uptake capacity of a solid phase of the tissue dressing material is less than 100% by weight.

15. A method of treating a tissue of a patient, comprising a step of
applying a liquid tissue dressing material in contact with the tissue of the patient, the tissue dressing material being an aqueous mixture, the tissue dressing material comprising at least 50% by weight of the combination of all constituents other than water, native chitosan, having a degree of acetylation below 2.5%, wherein the tissue dressing material has a pH above 4.5.

16. The method of claim 14 or 15 wherein the method of treating is locally confined antibacterial treatment of the patient's tissue.

* * * * *